United States Patent
Fischell et al.

(10) Patent No.: US 6,591,137 B1
(45) Date of Patent: Jul. 8, 2003

(54) IMPLANTABLE NEUROMUSCULAR STIMULATOR FOR THE TREATMENT OF GASTROINTESTINAL DISORDERS

(75) Inventors: David R. Fischell, Fair Haven, NJ (US); Adrian R. M. Upton, Hamilton (CA)

(73) Assignee: NeuroPace, Inc., Mountain View, CA (US)

( * ) Notice: Subject to any disclaimer, the term of this patent is extended or adjusted under 35 U.S.C. 154(b) by 168 days.

(21) Appl. No.: 09/710,194

(22) Filed: Nov. 9, 2000

(51) Int. Cl.[7] .................................................. A61N 1/36
(52) U.S. Cl. ............................ 607/40; 607/72; 607/133
(58) Field of Search .............................. 607/40, 41, 45, 607/46, 72–74, 133, 116, 138, 148

(56) References Cited

U.S. PATENT DOCUMENTS

| 5,690,691 A | * 11/1997 | Chen et al. .................... 607/40 |
| 5,861,014 A | * 1/1999 | Familoni ...................... 607/40 |
| 6,016,449 A | * 1/2000 | Fischall et al. ............... 607/45 |
| 6,026,326 A | * 2/2000 | Bardy .......................... 607/40 |

* cited by examiner

Primary Examiner—Mark Paschall

(57) ABSTRACT

A system and method for treating gastrointestinal and other disorders via electrical stimulation of plural portions of a patient's gastrointestinal tract uses an implantable control module, sensors attached to various structures of the gastrointestinal tract, and electrodes also attached to various structures of the gastrointestinal tract. Signals received from the sensors are analyzed to identify events in the gastrointestinal system, and electrical stimulation is applied to structures of the gastrointestinal tract, in sequence, to restore normal function or achieve other clinically desirable results.

38 Claims, 2 Drawing Sheets

IMPLANTABLE NEUROMUSCULAR STIMULATOR FOR THE TREATMENT OF GASTROINTESTINAL DISORDERS

FIELD OF THE INVENTION

This invention is in the field of devices for the treatment of gastrointestinal disorders in human subjects.

BACKGROUND OF THE INVENTION

At least 8% of the population has acid reflux, also known as gastroesophageal reflux disease (GERD), that is not controlled by the current treatment of choice—ion pump inhibitors that block acid production and other medications that affect contraction of the esophagus and gastroesophageal sphincter.

Some patients may experience transitory relaxations, typically of 5 to 35 seconds in duration (see Dent, J., Patterns of lower esophageal sphincter function associated with gastroesophageal reflux., Am. J. Med., Nov. 24, 1997; 103(5A): 29S–32S) of the gastroesophageal sphincter (GES, also known as the lower esophageal sphincter, or LES); this is the most common cause of reflux of acid and secretions from the stomach up into the lower esophagus. Armenian, B., Transitory relaxation of the esophageal inferior sphincter and gastroesophageal reflux, Rev Med. Suisse Romande, 1997; 117(10): 797–9. This reflux of secretions may cause pain and an increase in the risk of cancer of the esophagus even with use of medications.

Surgery is currently the only remaining choice for those who fail to respond to these medications. The results of surgery are often unsatisfactory. Other gastrointestinal disorders also involve disturbances of motility and sequential coordinated contraction from the esophagus to the lower bowel.

These disorders are frequently a result of a combination of lifestyle, excessive weight, and the effects of other medications (e.g. narcotics, antihypertensive, anti-inflammatories). The main problem is lack of sequential action of the gut musculature (e.g. loss of gastrocolic reflex due to diabetes, neuropathies, and medications such as narcotics, tranquilizers, and antidepressants).

Attempts to correct this problem have largely failed due to failure to consider coordinated sequential action of the GI tract.

Familoni et al. have shown in the dog model that the optimal frequency for stimulating stomach contraction is at four to five times the intrinsic rate of five cycles per minute. Familoni, B. O. et al., Electrical stimulation at a frequency higher than basal rate in human stomach, Dig. Dis. Sci., 1997 May; 42(5): 892–7. For the stomach, stimulation of one part will produce appropriate contraction of the whole stomach because the stomach acts as a syncytium (an integrated whole). While recent results of stimulation of the stomach in dogs have demonstrated efficacy in achieving motility (see Mintchev, M. P. et. al, Microprocessor-controlled movement of solid gastric content using sequential neural electrical stimulation, Gastroenterology, 2000 February; 118(2): 258–63), no implantable system has been envisioned to responsively stimulate the normal sequential action of more than a single segment of the gastrointestinal tract. To be successful in alleviating human gastrointestinal tract disorders, a treatment will often need to stimulate two or more segments of the gastrointestinal tract.

Numerous medications have been developed to suppress appetite or attempt to speed up the metabolism to treat obesity. None has been proven to be sufficiently specific or substantially free from side effects. Electrical stimulation of the brain to suppress or increase appetite has been shown in animals but the localization of the stimulation within the hypothalamus or other desired location is extremely difficult. There is ongoing work to determine if vagus nerve stimulation can successfully suppress appetite.

Fischell et al. in U.S. Pat. No. 6,016,449 describe a responsive programmable neurostimulator for the treatment of neurological events but does not describe the programming and techniques necessary for the treatment of gastrointestinal disorders.

Chen et al. in U.S. Pat. No. 5,690,691 describes a technique for pacing of the stomach and small intestine using phased stimulation with multiple electrodes, but does not consider using significant delays between stimulation of one organ and the next to emulate normal gastrointestinal tract function.

Familoni in U.S. Pat. No. 5,861,014 describes a system to sense and identify abnormal stomach electrical signals and to stimulate the stomach responsively to treat the detected gastric rhythm abnormalities. Familoni does not disclose the use of a system that involves the esophageal sphincter and would work for acid reflux, nor does he disclose the detecting of normal function and the use of the detected delays in normal gastrointestinal tract function to set the delays for triggering successive stimulation of gastrointestinal tract organs.

Bourgeois in U.S. Pat. No. 6,026,326 describes primarily enhancements to the Familoni invention for treating gastric rhythm abnormalities.

SUMMARY OF THE INVENTION

The present invention envisions an implantable neuromuscular stimulator with multiple (two or more) outputs producing sequential, prolonged pulses of 0.5 msec to 5 msec. Sequential and appropriate activation of the GI tract is produced by electrical stimulation pulses that are timed at intervals consistent with normal patterns of GI tract function for the specific spacing of the electrodes. In addition to creating gastrointestinal tract function similar to normal, this process has the potential to reeducate the GI tract to function near to normal patterns without stimulation. There is also good evidence that acid reflux can eventually cause esophageal cancer (after Barrett's esophagus, a complication of GERD that frequently leads to esophageal cancer) and the presence of reflux seems to interfere with the normal pattern of GI function all the way to the bowel.

Important areas for electrode placement include the upper esophagus, lower esophageal sphincter, stomach, duodenum, small intestine (optional) and the large bowel (colon—optional).

The present invention is a neuromuscular stimulator for sequential responsive stimulation to restore normal GI function. The most likely scenario for treating acid reflux will involve electrodes placed at the esophageal sphincter and stomach wall. When initiated, the stimulator will close the esophageal sphincter and start a timer. At the end of a preset time (e.g. 0.5–2 hours) the stomach electrodes will be energized to empty the stomach. At the end of a follow on period of time, at which the stomach should now be empty, the device will turn off all stimulation and be ready for the next sequence. Stimulation may be patient initiated from external device. This device may include buttons for initiating the sequence of stimulation and buttons for temporary suspension of the program to allow snacking.

For specific patterns of electrical activity associated with eating a meal the sequence can begin automatically when no food has passed through the esophagus for a preset period of time (e.g. 10 min). Eating or drinking is easily characterized by a higher frequency of swallowing than is typical of just normal saliva swallowing. After the meal is over and the sequence has been started, if additional food or drink or just normal saliva swallowing is detected by signals picked up by an electrode on the esophagus, the system may go into suspend mode for a specified period of time (e.g. 1 to 10 sec).

The stimulator would typically involve two to four electrodes acting as sensing and/or stimulating electrodes.

The control module will have data recording capabilities and a physician's workstation similar to that described by Fischell et. al in U.S. Pat. No. 6,016,449. The physician's workstation would have the capability to retrieve the data recorded by the control module and to program the specific functionality of the control module including parameters for stimulation and detection of gastrointestinal tract function.

It is also envisioned that additional types of sensors other than electrodes may be used for identifying motion or actions by parts of the gastrointestinal tract. These additional sensors could include temperature sensors, motion sensors (accelerometers) and pressure sensors to sense pressure within a gastrointestinal tract structure or pressure changes caused by expansion or contraction of a gastrointestinal tract structure.

Applying electrical stimulation to the gastrointestinal tract can have the effect of suppressing appetite but more important still is the potential of electrical stimulation of the gastrointestinal tract to produce "intestinal hurry" where the food is passed through the gastrointestinal tract more quickly than normal so as to reduce the body's absorption of nutrients. Gastrointestinal tract hurry can be produced by stimulation of the stomach and/or small intestine. The closed loop system envisioned would detect food being swallowed and/or stomach activity and responsively stimulate the gastrointestinal tract to increase the speed of passage of food through the small intestine. This technique should be less invasive than current surgical methods to reduce nutrient uptake and if not successful, surgery can still be performed.

Gastrointestinal tract stimulation according to the invention may be continuous, intermittent, or responsive to patient initiation or gastrointestinal tract activity detection.

Thus it is an object of the invention to have a system for restoration of normal gastrointestinal tract function by sequential stimulation signals applied to two or more electrodes placed on or near the structures of the gastrointestinal tract.

Another object of this invention is to use the sensing of gastrointestinal tract activity to initiate responsive stimulation to the gastrointestinal tract.

Another object of this invention is to use sensing of gastrointestinal tract activity to set the timing of sequential stimulation of the gastrointestinal tract.

Still another object of this invention is to have a system of electrodes connected by leads to a control module, the entire system being placed under the skin and being essentially contained within the abdomen.

Still another object of this system is to have data recording capability within the control module.

Yet another object of the present invention is to have external equipment including a patient initiating device.

Yet another object of the present invention is to have external equipment including a physician's workstation for reading out recorded data and programming the gastrointestinal tract stimulator.

Still another object of the system is to sense sphincter contraction or relaxation in order to activate electrical stimulation of the sphincter.

Still another object of the system is to sense sphincter contraction and augment or assist this with electrical stimulation and/or trigger assistance from an artificial sphincter. This has applications for any sphincter system (e.g. gastroesophageal, pyloric, anal, bladder or urethra).

Yet another object of the present invention is to stimulate the stomach and/or small intestine to produce gastrointestinal hurry where the speed of the passage of food through the gastrointestinal tract is increased so as to reduce the absorption of nutrients as a means to achieve weight loss for obese patients.

These and other objects and advantages of this invention will become apparent to a person of ordinary skill in this art upon careful reading of the detailed description of this invention including the drawings as presented herein.

DETAILED DESCRIPTION OF THE DRAWINGS

Figure 1:
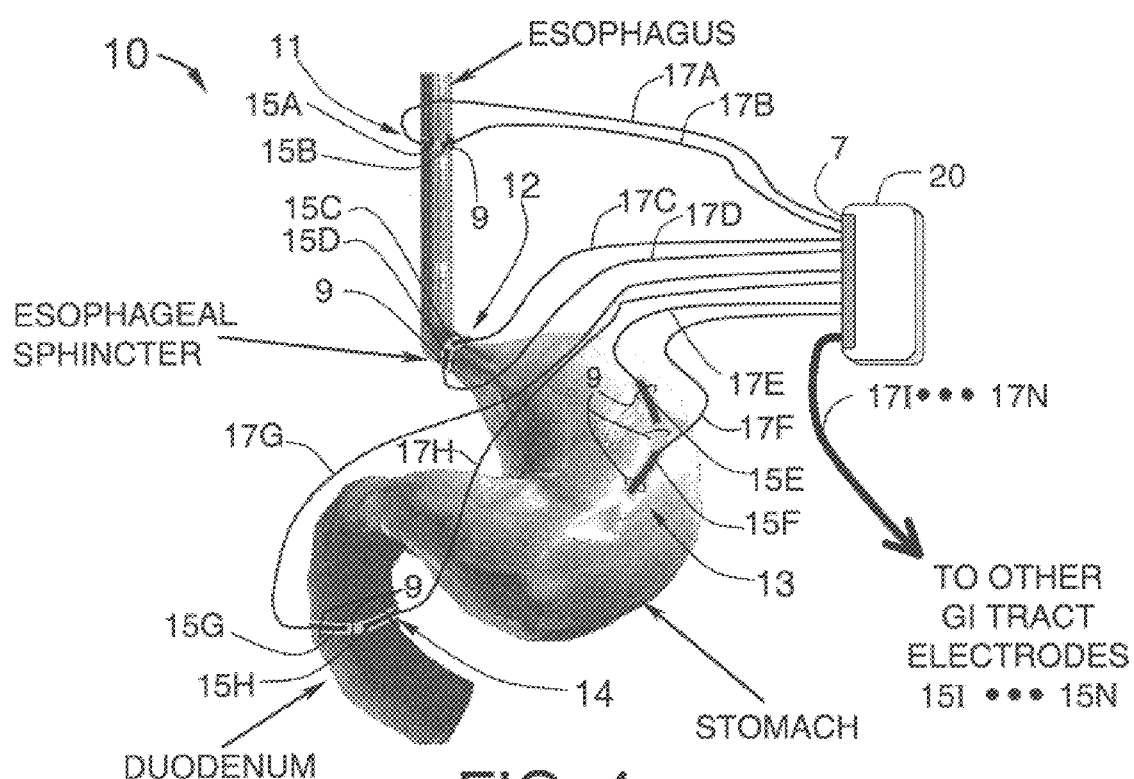
FIG. 1 is a sketch of a portion of the human gastrointestinal tract, having an implanted stimulator control module with attached electrodes.

FIG. 1 illustrates the configuration of an implantable system 10 for the treatment of gastrointestinal disorders as it would be implanted under the skin of a human body, the system including a control module 20, electrodes 15A, 15B, 15C, 15D, 15E, 15F, 15G, and 15H with leads 17A, 17B, 17C, 17D, 17E, 17F, 17G, and 17H connected through a connector 7 to the control module 20. It is envisioned that the control module 20 is permanently implanted into the patient's abdomen. It is also envisioned that the control module 20 could be located in the patient's chest like a heart pacemaker or in the patient's abdominal wall. Each of the electrodes 15A through 15H would be placed at a specific site along the patient's GI tract. The connecting leads 17A through 17H would be run from the control module 20 underneath the skin and then be connected to the electrodes 15A through 15H. Although FIG. 1 shows only eight active electrodes 15A, 15B, 15C, 15D, 15E, 15F, 15G, and 15H with connecting leads 17A, 17B, 17C, 17D, 17E, 17F, 17G, and 17H, more than eight active electrodes with connecting leads may be used with the present invention.

FIG. 1 specifically shows electrode sets 11, 12, 13 and 14 as follows: Electrode set 11 with electrodes 15A and 15B is located on the esophagus between the esophageal sphincter and the mouth. The electrodes 15A and 15B are connected to the control module 20 by the leads 17A and 17B. Sutures 9 surgically placed during system implantation, hold the electrodes 15A and 15B against the surface of the esophagus. Although two electrodes 15A and 15B are shown here for the electrode set 11, more than two electrodes or a single electrode referenced to a common ground (such as the case of the control module 20) may be used. The electrode set 11 is used with the present invention for detection of food or liquid passing through the esophagus. It is also known that electrical stimulation of the esophagus well above the esophageal sphincter will cause the esophageal sphincter to open. Thus if necessary, responsive stimulation of electrode set 11 can be used to open the esophageal sphincter to allow food to pass into the stomach.

Electrode set 12 with electrodes 15C and 15D is located on the esophageal sphincter between the esophagus and the stomach. The electrodes 15C and 15D are connected to the control module 20 by the leads 17C and 17D. Sutures 9 surgically placed during system implantation, hold the electrodes 15C and 15D against the surface of the esophagus. Although two electrodes 15C and 15D are shown here for the electrode set 12, more than two electrodes or a single electrode referenced to a common ground such as the case of the control module 20 may be used. The electrode set 12 is used with the present invention to provide electrical stimulation to maintain closure of the esophageal sphincter. Such closure will prevent acid reflux. It is most important to maintain closure of the esophageal sphincter during the time that the stomach is working to digest food. It is also envisioned that electrode set 12 can be used as a "power assist" device to sense inadvertent relaxation of the esophageal sphincter and apply stimulation responsively to keep it closed.

Electrode set 13 with electrodes 15E and 15F is located on the surface of the stomach. The electrodes 15E and 15F are connected to the control module 20 by the leads 17E and 17F. Sutures 9, surgically placed during system implantation, hold the electrodes 15E and 15F against the surface of the stomach. Although two electrodes 15E and 15F are shown here for the electrode set 13, more than two electrodes or a single electrode referenced to a common ground such as the case of the control module 20 may be used. The electrode set 13 is used with the present invention to provide electrical stimulation to encourage speedy digestion of food by the stomach during which the electrode set 12 will keep the esophageal sphincter closed to avoid acid reflux. The electrode set 13 can also be used to produce gastrointestinal hurry speeding the passage of food through the gastrointestinal tract to reduce nutrient uptake for obese patients.

Electrode set 14 with electrodes 15G and 15H is located on the surface of the duodenum. The electrodes 15G and 15H are connected to the control module 20 by the leads 17G and 17H. Sutures 9 surgically placed during system implantation, hold the electrodes 15G and 15H against the surface of the stomach. Although two electrodes 15G and 15H are shown here for the electrode set 14, more than two electrodes or a single electrode referenced to a common ground such as the case of the control module 20 may be used. The electrode set 14 is used with the present invention to provide electrical stimulation to encourage contraction of the duodenum to assist in emptying the stomach during which the electrode set 12 will keep the esophageal sphincter closed to avoid acid reflux. The electrode set 14 can also be used to produce gastrointestinal hurry speeding the passage of food through the gastrointestinal tract to reduce nutrient uptake for obese patients.

Throughout the detailed description of the present invention, the terminology "the electrodes 15A through 15N" is meant to include all electrodes 15A, 15B, 15C, ... to 15N, inclusive, where N may be any integer greater than or equal to 1. Similar terminology using the words "through" or "to" for other groups of objects (i.e., leads 17A through 17N) will have a similar inclusive meaning.

The control module 20 is also shown connected to leads 17I through 17N that connect to additional gastrointestinal tract electrodes 15I through 15N. The electrodes 15I through 15N may be located on the small intestine, large intestine and/or bowel as needed to properly stimulate normal function of the entire gastrointestinal tract.

Each electrode 15A through 15N can be used for either sensing electrical signals from the gastrointestinal tract or for stimulating the gastrointestinal tract to cause the opening or closing of the esophageal sphincter or contractions of digestive organs like the stomach, duodenum, small intestine, large intestine or bowel. While direct stimulation to gastrointestinal tract portions such as the esophageal sphincter will cause it to contract, stimulation to the upper esophagus will cause relaxation of the esophageal sphincter. The combination of sensing with timed stimulation allows the system 10 the ability to replicate normal gastrointestinal tract function. The system in many cases would work like a demand pacemaker, i.e. when a specific gastrointestinal tract organ is functioning normally, it is not stimulated, but when it fails to function properly, stimulation is applied. For example during digestion by the stomach if the esophageal sphincter is not closed, acid reflux can occur. Sensing that the stomach is actively digesting food and the esophageal sphincter is open as a neurological event that would induce a responsive stimulation by the control module 20 through the leads 17C and 17D to the electrodes 15C and 15D to close the esophageal sphincter.

Typical stimulation signals to close the esophageal sphincter would be one to 30 biphasic pulses over a 1 second period repeating every 5 to 60 seconds, each pulse being between 0.5 and 2 milliseconds long. The peak-to-peak voltage and current should be between 1 to 25 volts (peak to peak) and 1 to 20 milliamps.

For emptying the stomach, Lin et al. have shown that 4 milliamp pulses of 300 ms duration applied to the stomach work well. Lin, Z. Y. et al., Effects of pacing parameters on entrainment of gastric slow waves in patients with gastroparesis, Am. J. Physiol., 1998 January; 274(1 Pt 1): G186–91. Mintchev et al. report that 50 Hz 14 volt signals are effective. Mintchev, M. P. et al., Microprocessor controlled movement of liquid gastric content using sequential neural electrical stimulation, Gut, 1998 November; 43(5): 607–11. Ideally, one should stimulate the stomach at a frequencies at least 10% above that of the intrinsic gastric slow wave frequency. With such stimulation, typical stomach emptying times are between 5 and 10 minutes as compared to normal stomach emptying times of 20 to 30 minutes. Similar pulse trains sent over the leads 17E and 17F to stomach electrodes 15E and 15F would be effective in stimulating muscular contractions of the stomach to digest and expel digested food.

It is envisioned that each organ can be stimulated in sequence with appropriate delays set to emulate the normal delays associated with movement of food through the gastrointestinal tract. For example, when food is sensed by electrode set 11, any stimulation of the electrode set 12 is immediately stopped to allow the esophageal sphincter to open. The intensity and frequency of the signals received by the control module 20 from the esophagus electrodes 15A and 15B can allow differentiation of a saliva swallow from a meal. Eating or drinking is easily characterized by a higher frequency of swallowing than is typical of just normal saliva swallowing. Once a period of 5 to 60 seconds have passed without significant swallowing, the esophageal sphincter would be closed (if needed) by stimulation of the electrode set 12. After a delay of between 30 minutes and 3 hours, if the stomach is not actively contracting to digest the food, stimulation of the electrodes set 13 would begin and go on for a period of 30 to 100 minutes. Additional stimulation of electrode set 14 on the duodenum would commence between 5 and 30 minutes after the stomach stimulation begins. In this way each stimulation function is sequential with appropriate delays so as to closely resemble normal gastrointestinal tract function, but with delays, durations, and sequences modified as desired to achieve advantageous clinical results.

Initiation of the gastrointestinal tract stimulation can be automated or can be initiated by the patient by use of an external device that can send signals to the control module 20. See, for example, the external data interface illustrated in FIG. 2 of U.S. Pat. No. 6,016,449 to Fischell, et al.; an external magnet coupled with a magnetic field detector in the control module 20 might also be used in an embodiment of the invention. Also the patient would have the capability to override the system to cause contraction or relaxation at any time.

The appropriate delays and settings for each patient may be different. It is envisioned that in patients with occasional normal gastrointestinal tract function, that recordings of the sequence of muscle contractions in the gastrointestinal tract can be stored by the control module and used by the physician to determine the appropriate stimulation delays and settings. A completely automated system is also envisioned that would analyze the delays associated with normal gastrointestinal tract function and automatically set appropriate stimulation parameters.

It is also envisioned that other types of sensors other than electrodes may be used for identifying motion or actions by parts of the gastrointestinal tract. These additional sensors could include temperature sensors, motion sensors (accelerometers) and pressure sensors to sense pressure within a gastrointestinal tract structure or pressure changes caused by expansion or contraction of a gastrointestinal tract structure.

The sensory system can utilize electrical activity of muscle or mechanical changes in the size of the gut. For example, electrodes might be placed in an expandable matrix such that the distance between electrodes or the curvature of the electrodes sensed by changes in inductance or capacitance could signal contraction or relaxation of the underlying muscle.

Figure 2:
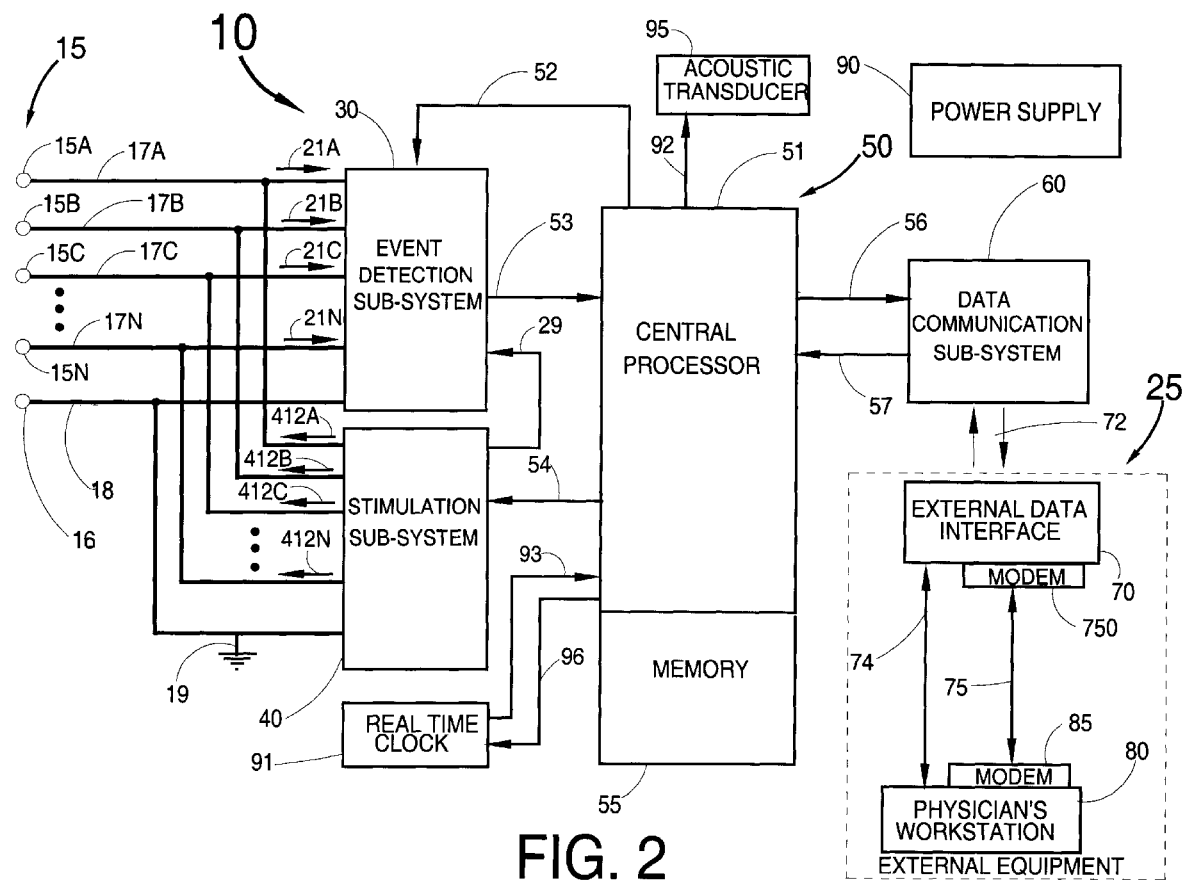
FIG. 2 is a block diagram of the electronic circuitry of the implanted control module illustrated in FIG. 1.

Throughout FIGS. 1 and 2, lines connecting boxes on block diagrams or on software flow charts will each be labeled with an element number. Lines without arrows between boxes or other elements shall indicate a single lead.

Lines with arrows connecting boxes or other elements are used to represent any of the following:

1. A physical connection, namely a lead or group of leads (data bus) over which analog or digital signals may be sent.
2. A data stream sent from one hardware element to another. Data streams include messages, analog or digital signals, commands, neural electrical signals, and software downloads to change system operation and parameters.
3. A transfer of information between software modules. Such transfers include software subroutine calls with and without the passing of parameters, and the reading and writing of memory locations.

In each case, the descriptive text herein will indicate each specific use of a line with an arrow.

FIG. 2 is a block diagram of the implantable system 10 and the external equipment 11. The leads 17A through 17N from the electrodes 15A through 15N, and the lead 18 from a common electrode 16, are shown connected to both an event detection sub-system 30 and a stimulation sub-system 40. In one embodiment of the invention, it is also envisioned to use the case of the control module 20 of FIG. 1 as the common (or indifferent) electrode 16. The leads 17A through 17N carry EEG signals 21A through 21N from the electrodes 15A through 15N to the event detection sub-system 30. The electrodes 15A through 15N can be energized by the stimulation sub-system 40 via the leads 17A through 17N to electrically stimulate the patient's GI tract using the stimulation signals 412A through 412N respectively. Although the electrodes 15A through 15N and 16 shown here are connected to both the event detection sub-system 30 and the stimulation sub-system 40, it should be apparent that a separate set of electrodes and associated leads could be used with each sub-system. Furthermore, it is envisioned that any one or more of the electrodes 15A through 15N could be electrically connected (i.e., shorted) to the electrode 16 or to each other. This would be accomplished by appropriate switching circuitry in the stimulation sub-system 40.

It is envisioned that instead of electrodes 15A through 15N, one or more of the leads 17A through 17N could instead be connected to other types of sensors. These additional sensors could include temperature sensors, motion sensors (accelerometers) and pressure sensors to sense pressure within a gastrointestinal tract structure or pressure changes caused by expansion or contraction of a gastrointestinal tract structure.

The event detection sub-system 30 receives neural electrical signals 21A through 21N (referenced to a system ground 19 connected to the lead 18 from the common electrode 16) and processes them to identify gastrointestinal events such as a swallowing. A central processing system 50 with a central processor 51 and memory 55 acts to control and coordinate all functions of the implantable system 10. A first interconnection 52 is used to transmit programming parameters and instructions to the event detection sub-system 30 from the central processing system 50. A second interconnection 53 is used to transmit signals to the central processing system 50 identifying the detection of a neurological event by the event detection sub-system 30. The second interconnection 53 is also used to transmit EEG and other related data for storage in the memory 55.

When an event is detected by the event detection sub-system 30 (by processing such as that disclosed and described in U.S. Pat. No. 6,016,449 to Fischell, et al., referenced above), the central processor 51 can command the stimulation sub-system 40 via a third interconnection 54 to transmit electrical signals to any one or more of the electrodes 15A through 15N via the leads 17A through 17N. It is anticipated that, if appropriate, electrical signals 412A to 412N, inclusive, are transmitted to certain locations along the GI tract, a normal GI tract function can be produced. It may also be necessary for the stimulation sub-system 40 to temporarily disable the event detection sub-system 30 via a fourth interconnection 29 when stimulation is imminent so that the stimulation signals are not inadvertently interpreted as a neurological event by the event detection sub-system 30.

The stimulation sub-system 40 may also be engaged to perform continuous or periodic stimulation to one or more of the GI tract electrodes 15A through 15N, inclusive. These signals may be used for example to keep the esophageal sphincter closed during stomach food processing or to prevent acid reflux. In one embodiment of the invention, electrical stimulation from the stimulation sub-system 40 can include any of a wide range of frequencies from approximately 2 Hz to approximately 200 Hz. Details of a signal generator capable of generating waveforms over such a frequency range are well known in the art of electronics design.

A power supply 90 provides power to each component of the system 10. Power supplies for comparable implantable devices such as heart pacemakers and heart defibrillators are well known in the art of implantable electronic devices. Such a power supply typically utilizes a primary (non-rechargeable) storage battery with an associated d-c to d-c converter to obtain any voltages required for the implantable system 10. However, it should be understood that in an alternative embodiment of the invention, the power supply could use a rechargeable battery that is charged by means of a coil of wire in the control module 20 that receives energy by magnetic induction from an external coil that is placed outside the patient but in close proximity to the control module 20. The implanted coil of wire could also be located remotely from control module 20 but joined to it by electrical leads. Such technology is well known from the rechargeable cardiac pacemaker. Furthermore, the same pair of coils of wire could be used as inductive transducers to provide power to the implanted system 10 when it is desired to read out stored telemetry, reprogram some portion of the implanted system 10, or replenish a rechargeable battery.

The central processing system 50 is connected to a data communication sub-system 60, thereby allowing data stored in the memory 55 to be retrieved by the patient's physician via a wireless communication link 72. An external data interface 70 can be directly connected to the physician's workstation 80 via a traditional serial data connection 74 (such as an RS-232 interface). Alternately, the serial connection may be made trans-telephonically, via modems 85 and 750 and a phone line 75 from the patient's home to the physician's workstation 80. Software in the computer section of the physician's workstation 80 allows the physician to read out a history of events detected by the implantable system 10, including neural signal information. In a preferred embodiment of the invention, the physician's workstation 80 also allows the physician to specify or alter any programmable parameters of the implantable system 10.

As shown in FIGS. 1 and 2, a buzzer 95 connected to the central processor 51 via a link 92 can be used to notify the patient that a neurological event has occurred, the implanted system 10 is about to deliver stimulation, or that the implanted system 10 is not functioning properly. In alternative embodiments, the buzzer could provide a mechanical vibration (typically an acoustic signal) or an electrical stimulation "tickle," either of which could be perceived by the patient.

A real time clock 91 is used for timing and synchronizing various portions of the implanted system 10 and also to enable the system to provide the exact date and time corresponding to each neurological event that is detected by the implantable system 10 and recorded in the memory 55. A fifth interconnection 96 is used to send data from the central processor 51 to the real time clock 91 in order to set the correct date and time in the clock 91.

The various interconnections between sub-systems (e.g., the illustrated interconnections 29, 52, 53, 54, 56, 57, 92, 93 and 96) may be either analog or digital, single wire or multiple wires (a "data bus").

In a preferred embodiment of the invention, the operation of the system 10 of FIG. 2 for detecting and treating gastrointestinal tract dysfunction would typically be as follows:

1. The event detection sub-system 30 continuously processes the signals 21A through 21N carried by the leads 17A through 17N from the N electrodes 15A through 15N.

2. When an event is detected (e.g. a swallow), the event detection sub-system 30 notifies the central processor 51 via the second interconnection 53 that an event has occurred.

3. The central processor 51 then identifies the appropriate stimulation action and time delay and after the delay triggers the stimulation sub-system 40 via the third interconnection 54 to electrically stimulate the patient's gastrointestinal tract with electrical signals in order to activate appropriate gastrointestinal tract function, using any one, several or all of the electrodes 15A through 15N. For example, a sequence of sending a signal to electrodes 15Ca and 15D of FIG. 1 stimulating the esophageal sphincter to close, a delay of 20 minutes followed by stimulation of the stomach with 300 ms long 4 milliamp pulses at 10 pulses per minute for 30 minutes could follow the detection of multiple swallows within a 2 minute period from an esophageal sensor such as the electrodes 15A and 15B of FIG. 1.

4. During stimulation, the stimulation sub-system 40 also sends a signal via the fourth interconnection 29 to the event detection sub-system 30 to disable event detection during stimulation to avoid an undesired input into the event detection sub-system 30.

5. The central processor system 50 will store received sensor signals and event related data received from the event detection sub-system 30 via the second interconnection 53 over a time from X minutes before the event to Y minutes after the event for later analysis by the patient's physician. The value of X and Y may be set from as little as approximately 0.1 minutes to as long as approximately 2 hours.

6. The central processor 51 may generate a "buzz" to notify the patient that an event has occurred and the system is working by sending a signal via the link 92 to the buzzer 95.

Additional objects and advantages of the present invention will become apparent to those skilled in the art to which this invention relates from the subsequent description of the preferred embodiments and the appended claims, taken in conjunction with the accompanying drawings.

What is claimed is:

1. A system for treating a gastrointestinal tract disorder in a human patient, the system comprising:
    an implantable control module including electronic circuitry;
    a plurality of electrodes connected to the electronic circuitry, wherein the electrodes are adapted to be placed on a portion of the patient's gastrointestinal tract, the portion comprising a first plurality of gastrointestinal tract structures; and
    wherein the electronic circuitry of the control module is adapted to electrically stimulate a second plurality of gastrointestinal tract structures in a coordinated sequence with at least one time delay between structures of the second plurality, the stimulation being applied to reinforce a desired sequential function in the portion of the patient's gastrointestinal tract.

2. The system of claim 1, wherein one electrode of the plurality of electrodes comprises a common electrode.

3. The system of claim 1, wherein the portion of the patient's gastrointestinal tract includes the esophagus, and at least one electrode is located on the esophagus.

4. The system of claim 1, wherein the portion of the patient's gastrointestinal tract includes the esophageal sphincter, and at least one electrode is located on the esophageal sphincter.

5. The system of claim 1, wherein the portion of the patient's gastrointestinal tract includes the stomach, and at least one electrode is located on the stomach.

6. The system of claim 1, wherein the portion of the patient's gastrointestinal tract includes the duodenum, and at least one electrode is located on the duodenum.

7. The system of claim 1, wherein the portion of the patient's gastrointestinal tract includes the small intestine, and at least one electrode is located on the small intestine.

8. The system of claim 1, wherein the portion of the patient's gastrointestinal tract includes the large intestine, and at least one electrode is located on the large intestine.

9. The system of claim 1, wherein the portion of the patient's gastrointestinal tract includes the bowel, and at least one electrode is located on the bowel.

10. The system of claim 1, further comprising external equipment, the external equipment capable of two-way data communication with the electronic circuitry of the control module.

11. The system of claim 7, wherein the external equipment is a patient's initiating device.

12. The system of claim 7, wherein the electronic circuitry of the control module is adapted to be programmed by the external equipment.

13. The system of claim 12, wherein the external equipment is capable of programming at least one parameter of the electronic circuitry of the control module.

14. The system of claim 7, wherein the control module is adapted to record data.

15. The system of claim 14, wherein the external equipment is capable of receiving the data recorded by the control module.

16. The system of claim 1, further comprising at least one sensor adapted to be placed on the portion of the patient's gastrointestinal tract, the sensor being capable of sensing activity within the gastrointestinal tract.

17. The system of claim 16, wherein stimulation is initiated in response to a signal received from the at least one sensor.

18. The system claim 16, wherein the at least one sensor is an electrode capable of detecting neuromuscular electrical activity.

19. The system claim 16, wherein the at least one sensor is a motion sensor capable of detecting motion of a structure of the gastrointestinal tract.

20. The system claim 16, wherein the at least one sensor is a pressure sensor capable of detecting expansion or contraction of a structure of the gastrointestinal tract.

21. The system claim 16, wherein the at least one sensor is a pressure sensor capable of detecting the pressure within a structure of the gastrointestinal tract.

22. The system claim 16, wherein the at least one sensor is a temperature sensor capable of detecting the temperature within a structure of the gastrointestinal tract.

23. The system of claim 16, wherein at the electrical circuitry of the control module comprises an event detector, wherein the event detector is capable of analyzing input from the at least one sensor to identify a specific activity within the gastrointestinal tract.

24. The system of claim 23 wherein the specific activity within the gastrointestinal tract detected by the event detector is swallowing by the patient.

25. The system of claim 23 wherein the specific activity within the gastrointestinal tract detected by the event detector is stomach contraction.

26. The system of claim 23 wherein the specific activity within the gastrointestinal tract detected by the event detector is contraction of the esophageal sphincter.

27. The system of claim 23 wherein the electrical circuitry of the control module is adapted to identify a timing sequence corresponding to a normal sequential action of the structures of the gastrointestinal tract by analyzing an input from the at least one sensor.

28. The system of claim 27 wherein the electrical circuitry of the control module is adapted to generate a plurality of stimulation signals incorporating the at least one time delay, wherein the at least one time delay is set to correspond to the timing sequence corresponding to normal gastrointestinal tract action identified by the electrical circuitry of the control module.

29. The system of claim 27 wherein the electrical circuitry of the control module is adapted to generate a plurality of stimulation signals incorporating the at least one time delay, wherein the at least one time delay is set to accelerate the timing sequence corresponding to normal gastrointestinal tract action identified by the electrical circuitry of the control module.

30. The system of claim 23 wherein the electrical circuitry of the control module is adapted to generate an electrical stimulation signal in response to the identification of a specific activity within the gastrointestinal tract by the event detector, the electrical stimulation signal being transmitted to at least one of the plurality of electrodes.

31. The system of claim 30 wherein the electronic circuitry is adapted to delay for a preset time before generating the stimulation signal.

32. The system of claim 1, wherein the first plurality of gastrointestinal tract structures corresponds to the second plurality of gastrointestinal tract structures.

33. A method for treating a gastrointestinal tract disorder in a human patient with an implantable system including a control module including electronic circuitry, a plurality of electrodes connected to the electronic circuitry, wherein the electrodes are adapted to be placed on a portion of the patient's gastrointestinal tract, the portion comprising a plurality of gastrointestinal tract structures, and at least one sensor connected to the electronic circuitry, wherein the sensor is adapted to be placed on the portion of the patient's gastrointestinal tract and is capable of sensing activity within the gastrointestinal tract, the method comprising the steps of:

receiving a sensed signal from the at least one sensor, wherein the sensed signal is representative of activity within the gastrointestinal tract;

analyzing the sensed signal to identify an event in the gastrointestinal tract;

waiting for a time delay to elapse; and stimulating at least one electrode of the plurality of electrodes to restore normal function to the portion of the patient's gastrointestinal tract, wherein the at least one electrode is on a different structure of the plurality of gastrointestinal tract structures.

34. A system for treating gastroesophageal reflux disease (GERD) in a human patient, the system comprising:

an implantable control module including electronic circuitry;

a plurality of electrodes connected to the electronic circuitry, wherein the electrodes are adapted to be placed on a portion of the patient's gastrointestinal tract, the portion comprising a first plurality of gastrointestinal tract structures including the lower esophageal sphincter (LES); and wherein the electronic circuitry of the control module is adapted to electrically stimulate a second plurality of gastrointestinal tract structures including the LES in a coordinated sequence with at least one time delay between structures of the second plurality, the stimulation being applied to ensure closure of the LES during at least a portion of a digestion process and to reinforce a desired sequential function in the portion of the patient's gastrointestinal tract.

35. The system of claim 34, further comprising at least one sensor adapted to be placed on the portion of the patient's gastrointestinal tract, the sensor being capable of sensing activity within the gastrointestinal tract.

36. The system of claim 35, wherein the at least one sensor is placed on the patient's esophagus to detect swallowing.

37. The system of claim 36, wherein the electronic circuitry is adapted to temporarily suspend the stimulation of the LES when swallowing is detected, thereby allowing the LES to open.

38. A method for treating gastroesophageal reflux disease (GERD) in a human patient with an implantable system including a control module including electronic circuitry, a plurality of electrodes connected to the electronic circuitry, wherein the electrodes are adapted to be placed on a portion of the patient's gastrointestinal tract, the portion comprising a first plurality of gastrointestinal tract structures including the patient's lower esophageal sphincter (LES), and at least one sensor connected to the electronic circuitry, wherein the sensor is adapted to be placed on the patient's esophagus to detect swallowing, the method comprising the steps of:

electrically stimulating a second plurality of gastrointestinal tract structures including the LES in a coordinated sequence with at least one time delay, the stimulation being applied to ensure closure of the LES during at least a portion of a digestion process and to reinforce a desired sequential function in the portion of the patient's gastrointestinal tract;

receiving a sensed signal from the at least one sensor, wherein the sensed signal is representative of activity within the patient's esophagus;

analyzing the sensed signal to identify swallowing in the patient's esophagus; and temporarily suspending the stimulation of the LES when swallowing is identified, thereby allowing the LES to open.

* * * * *